(12) United States Patent
Sakurai et al.

(10) Patent No.: US 12,090,181 B2
(45) Date of Patent: Sep. 17, 2024

(54) BIFIDOBACTERIUM GENUS BACTERIUM

(71) Applicant: MORINAGA MILK INDUSTRY CO., LTD., Tokyo (JP)

(72) Inventors: Takuma Sakurai, Kanagawa (JP); Nanami Hashikura, Kanagawa (JP); Kanetada Shimizu, Kanagawa (JP); Sachiko Takahashi, Kanagawa (JP); Ayako Horigome, Kanagawa (JP)

(73) Assignee: Morinaga Milk Industry Co., Ltd., Tokyo (JP)

( * ) Notice: Subject to any disclaimer, the term of this patent is extended or adjusted under 35 U.S.C. 154(b) by 0 days.

(21) Appl. No.: 18/047,477

(22) Filed: Oct. 18, 2022

(65) Prior Publication Data

US 2023/0066928 A1 Mar. 2, 2023

Related U.S. Application Data

(62) Division of application No. 16/498,148, filed as application No. PCT/JP2018/011915 on Mar. 23, 2018, now Pat. No. 11,504,407.

(30) Foreign Application Priority Data

Mar. 28, 2017 (JP) ................ 2017-063324

(51) Int. Cl.
  *A61K 35/745* (2015.01)
  *A23C 9/123* (2006.01)
  *A23L 33/00* (2016.01)
  *A23L 33/135* (2016.01)
  *C12N 1/20* (2006.01)

(52) U.S. Cl.
  CPC .......... *A61K 35/745* (2013.01); *A23C 9/1234* (2013.01); *A23L 33/135* (2016.08); *A23L 33/40* (2016.08); *C12N 1/20* (2013.01); *A23V 2002/00* (2013.01); *A23V 2400/517* (2023.08); *A23V 2400/533* (2023.08)

(58) Field of Classification Search
  CPC ..... A61K 35/375; A23L 33/135; A23L 33/40; A23C 9/1234; C12N 1/20; A23V 2400/517; A23V 2400/533; A23V 2002/00
  See application file for complete search history.

(56) References Cited

U.S. PATENT DOCUMENTS

| | | |
|---|---|---|
| 2011/0223137 A1 | 9/2011 | Darmaun et al. |
| 2012/0207712 A1 | 8/2012 | Longoni et al. |
| 2014/0186409 A1 | 7/2014 | Lang et al. |
| 2014/0219982 A1 | 8/2014 | Matsubara et al. |
| 2021/0100852 A1 | 4/2021 | Sakurai et al. |

FOREIGN PATENT DOCUMENTS

| | | |
|---|---|---|
| EP | 3135754 A1 | 3/2017 |
| JP | 2012-510800 A | 5/2012 |
| JP | 2012-515167 A | 7/2012 |
| JP | 2014-513106 A | 5/2014 |
| JP | 2014-195433 A | 10/2014 |
| WO | WO2013/047082 A1 | 4/2013 |

OTHER PUBLICATIONS

International Search Report for PCT Patent App. No. PCT/JP2018/011915 (Jun. 19, 2018).
Zeng, Z., et al., "Bifidobacteria possess inhibitory activity against dipeptidyl peptidase-IV," Lett. Appl. Microbiol. 2015;62:250-255.
Candela, M., et al., "Plasminogen-dependent proteolytic activity in Bifidobacterium lactis," Microbiol. 2008;154:2457-2462.
Trivedi, M. S., et al., "Food-derived opioid peptides inhibit cysteine uptake with redox and epigenetic consequences," J. Nutr. Biochem. 2014;25(10):1011-1018.
Yan, T.-R., et al., "Catalytic Properties of X-Prolyl Dipeptidyl Aminopeptidase from *Lactococcus lactis* subsp. cremoris hTR," Biosci. Biotech. Biochem. 1992;56(5):704-707.
Sumi, H., et al., "Enhancement of the Fibrinolytic Activity in Plasma by Oral Administration of Nattokinase," Acta Haematol. 1990;84:139-143.
Yamamoto, K., Japanese Journal of Lactic Acid Bacteria, vol. 19, No. 1, 2008, with its partial English language translation thereof.
International Preliminary Report On Patentability for PCT Patent App. No. PCT/JP2018/011915 (Oct. 10, 2019).
Extended European Search Report for European Patent App. No. 18776670.4 (Nov. 24, 2020).
Loquasto, J. R., et al., "Short communication: The complete genome sequence of *Bifidobacterium animalis* subspecies animalis ATCC 25527 and comparative analysis of growth in milk with *B. animalis* subspecies lactis DSM 10140," J. Dairy Sci. 2011;94(12):5864-5870.
Anonymous: "Dipeptidyl peptidase IV (DPP IV) N-terminal region./Prolyl oligopeptidase family-*Bifidobacterium longum* subsp. longum F8-BIL_18920," 2010, XP55749538, 4 pp.
Examination Report No. 3 For Standard Patent Application for Australian Patent App. No. 2018242882 (May 25, 2021).

(Continued)

*Primary Examiner* — Robert A Zeman
(74) *Attorney, Agent, or Firm* — Cermak & McGowan LLP; Shelly Guest Cermak

(57) ABSTRACT

Novel *Bifidobacterium* bacteria having an opioid peptide decomposition action and a noncollagenous glycoprotein decomposition action are provided. The present invention relates to one or more kinds of *Bifidobacterium* bacteria selected from the group consisting of *Bifidobacterium bifidum* MCC1092 (NITE BP-02429), *Bifidobacterium bifidum* MCC1319 (NITE BP-02431), *Bifidobacterium bifidum* MCC1868 (NITE BP-02432), *Bifidobacterium bifidum* MCC1870 (NITE BP-02433), and *Bifidobacterium longum* subsp. *longum* MCC1110 (NITE BP-02430), as well as a composition for decomposing an opioid peptide and composition for decomposing a noncollagenous glycoprotein containing the *Bifidobacterium* bacteria as an active ingredient.

11 Claims, No Drawings

(56) References Cited

OTHER PUBLICATIONS

Huang, I.-N., et al., "New screening methods for probiotics with adhesion properties to sialic acid and sulphate residues in human colonic mucin using the Biacore assay," J. Appl. Microbiol. 2012;114(3):854-860.

Fujie, H., et al., "Toll-like receptor-2-activating bifidobacteria strains differentially regulate inflammatory cytokines in the porcine intestinal epithelial cell culture system: finding new anti-inflammatory immunobiotics," FEMS Immunol. Med. Microbiol. 2011;63(1):129-139.

Sugahara, H., et al., "Differences in folate production by bifidobacteria of different origins," Bioscience of Microbiota, Food and Health 2015;34(4):87-93.

BIFIDOBACTERIUM GENUS BACTERIUM

This application is divisional of U.S. patent application Ser. No. 16/498,148, filed Sep. 26, 2019, which is a national phase application under 35 U.S.C. § 371 of, International Application No. PCT/JP2018/011915, filed Mar. 23, 2018, and claims priority therethrough under 35 U.S.C. § 119 to Japanese Patent Application No. 2017-063324, filed Mar. 28, 2017, the entireties of which are incorporated by reference herein.

TECHNICAL FIELD

The present invention relates to novel *Bifidobacterium* bacteria and use thereof.

BACKGROUND ART

Opioid peptides are peptides that bind with an opioid receptor to express various physiological activities, and there are also many opioid peptides derived from foods. For example, it is known that an opioid peptide derived from milk and called β-casomorphin is produced from casein, which is milk protein, in the human alimentary tract. It is known that if such opioid peptides are not decomposed in the alimentary tract, they adversely affect living bodies in various ways. For example, it is known that opioid peptides derived from foods act on cells of the intestinal tract to inhibit absorption of cysteine, and thereby reduce the antioxidation ability (Non-patent document 1).

In order to avoid the influences of such opioid peptides, opioid peptides must be decomposed in the living bodies, and techniques therefor are investigated. For example, for the purpose of assisting digestion of opioid peptides derived from foods, there is disclosed an exogenous opioid peptide decomposition enzyme preparation, which comprises one or more ingredients selected from the group consisting of an enzyme preparation prepared from *Penicillium citrinum*, an enzyme preparation prepared from *Aspergillus oryzae*, and an enzyme preparation prepared from *Aspergillus melleus*, and shows decomposition activities for opioid peptides derived from wheat gluten and opioid peptides derived from casein (Patent document 1). Further, Non-patent document 2 discloses that an enzyme derived from *Lactococcus lactis* subsp. *cremoris* decomposes β-casomorphin, which is an opioid peptide derived from casein.

Further, noncollagenous glycoproteins constitute a class of cell adhesion molecules that form the reticular structure of the extracellular matrix surrounding cells or tissues, and as such proteins, there are known proteins that participate in the formation of thrombus, fibrinogen and fibronectin, laminin, and so forth. Such noncollagenous glycoproteins are decomposed by plasmin, which is a protease. Plasmin is a serine protease classified into endoprotease. Plasmin usually exists as plasminogen, which is an inactive precursor, in the living body, and it is activated by decomposition of a specific peptide bond of plasminogen by the plasminogen activator (PA), and exhibits the enzymatic activity as plasmin.

If the blood coagulation system is activated, fibrin is produced from fibrinogen, which is a noncollagenous glycoprotein, and fibrin clots are further formed. Plasmin has an activity of causing a phenomenon of decomposing and dissolving fibrin clots (fibrinogenolysis). That is, plasmin can dissolve a thrombus formed with fibrin clots, and therefore it is used for the fibrinolytic therapy, i.e., a conservative treatment for preventing or ameliorating conditions of ischemic injuries caused by thrombus (Non-patent document 3). Because of such usefulness of plasmin, materials and so forth having the plasmin activity are investigated, and for example, use of an enzyme derived from a bacterium and having the plasmin activity such as natto kinase has been reported (Non-patent document 4).

By the way, *Bifidobacterium* bacteria are known as anaerobic bacteria that inhabit in the human intestinal tract and give favorable influences such as intestinal regulation action and immunoregulation action to the hosts. It is known that *Bifidobacterium* bacteria produce and secrete various kinds of saccharide decomposition enzymes in order to maximize effective use of saccharides that reach the lower alimentary tract (Non-patent document 5). However, it is not known that *Bifidobacterium* bacteria have an enzymatic activity for decomposing such proteins as opioid peptides and noncollagenous glycoproteins.

PRIOR ART REFERENCES

Patent Document

Patent document 1: International Patent Publication WO2013/047082

Non-Patent Documents

Non-patent document 1: M. S. Trivedi et al., J. Nutr. Biochem., 25(10), pp. 1011-1018, 2014
Non-patent document 2: T-R Yan et al., Biosci. Biotech. Biochem., 56(5), pp. 704-707, 1992
Non-patent document 3: Takeshi Motomiya, CLINICIAN, No. 387, Vol. 37, pp. 73-841, 1990
Non-patent document 4: H. Sumi et al., Acta Haematol, 84, pp. 139-143, 1990
Non-patent document 5: Kenji Yamamoto, Jpn. J. Lactic Acid Bact., Vol. 19, No. 1, 2008

SUMMARY OF THE INVENTION

Object to be Achieved by the Invention

An object of the present invention is to provide novel *Bifidobacterium* bacteria having an opioid peptide decomposition action and noncollagenous glycoprotein decomposition action.

Means for Achieving the Object

The inventor of the present invention conducted various researches, and as a result, found that *Bifidobacterium* bacteria, cultures of the bacteria, and/or processed cell products of the bacteria have an enzymatic activity similar to that of dipeptidyl peptidase 4 (DPP-4), which has a decomposition activity for opioid peptides, and further have an enzymatic activity similar to that of plasmin, which has a decomposition activity for noncollagenous glycoproteins. They further found novel *Bifidobacterium* bacteria showing markedly higher such enzymatic activities compared with those of known *Bifidobacterium* bacteria, and accomplished the present invention.

Thus, the first aspect of the present invention is a novel *Bifidobacterium* bacterium, specifically, one or more kinds of *Bifidobacterium* bacteria selected from the group consisting of *Bifidobacterium bifidum* MCC1092 (NITE BP-02429), *Bifidobacterium bifidum* MCC1319 (NITE BP-02431), *Bifidobacterium bifidum* MCC1868 (NITE BP-02432), *Bifidobacterium bifidum* MCC1870 (NITE BP-02433), and *Bifidobacterium longum* subsp. *longum* MCC1110 (NITE BP-02430).

Another aspect of the present invention is an agent for decomposing an opioid peptide or composition for decomposing an opioid peptide, which contains the aforementioned novel *Bifidobacterium* bacterium, a culture of the bacterium, and/or a processed cell product of the bacterium as an active ingredient. In this aspect, the opioid peptide is preferably β-casomorphin.

Another aspect of the present invention is an agent for decomposing a noncollagenous glycoprotein or composition for decomposing a noncollagenous glycoprotein, which contains the aforementioned novel *Bifidobacterium* bacterium, a culture of the bacterium, and/or a processed cell product of the bacterium as an active ingredient. In this aspect, the noncollagenous glycoprotein is preferably fibrin, fibrinogen, fibronectin, laminin, or plasminogen.

Another aspect of the present invention is a pharmaceutical composition containing the aforementioned novel *Bifidobacterium* bacterium, a culture of the bacterium, and/or a processed cell product of the bacterium.

Another aspect of the present invention is a food or drink composition containing the aforementioned novel *Bifidobacterium* bacterium, a culture of the bacterium, and/or a processed cell product of the bacterium.

Effect of the Invention

The present invention provides a novel *Bifidobacterium* bacterium having an opioid peptide decomposition action and noncollagenous glycoprotein decomposition action.

The present invention further provides an agent for decomposing an opioid peptide or composition for decomposing an opioid peptide, a pharmaceutical composition for decomposing an opioid peptide, and a food or drink composition for decomposing an opioid peptide, which contain the aforementioned novel *Bifidobacterium* bacterium, a culture of the bacterium, and/or a processed cell product of the bacterium as an active ingredient. The agent for decomposing an opioid peptide or composition for decomposing an opioid peptide, pharmaceutical composition for decomposing an opioid peptide, and food or drink composition for decomposing an opioid peptide of the present invention can efficiently decompose opioid peptides, and therefore they can suppress absorption of opioid peptides that are ingested into a body and are not decomposed, from the alimentary tract.

The present invention also provides an agent for decomposing a noncollagenous glycoprotein or composition for decomposing a noncollagenous glycoprotein, a pharmaceutical composition for decomposing a noncollagenous glycoprotein, and a food or drink composition for decomposing a noncollagenous glycoprotein, which contain the aforementioned novel *Bifidobacterium* bacterium, a culture of the bacterium, and/or a processed cell product of the bacterium as an active ingredient. The agent for decomposing a noncollagenous glycoprotein or composition for decomposing a noncollagenous glycoprotein, pharmaceutical composition for decomposing a noncollagenous glycoprotein, and food or drink composition for decomposing a noncollagenous glycoprotein of the present invention can efficiently decompose noncollagenous glycoproteins.

Modes for Carrying Out the Invention

Hereafter, embodiments of the present invention will be explained. However, the present invention is not limited to the following embodiments, and can be freely embodied within the scope of the present invention. The percentages mentioned in this description are used on mass-basis unless especially indicated.

<*Bifidobacterium* Bacterium>

The first aspect of the present invention is an invention of a novel *Bifidobacterium* bacterium belonging to *Bifidobacterium bifidum* or *Bifidobacterium longum* subsp. *longum*, and specifically, it is *Bifidobacterium bifidum* MCC1092 (NITE BP-02429), *Bifidobacterium bifidum* MCC1319 (NITE BP-02431), *Bifidobacterium bifidum* MCC1868 (NITE BP-02432), *Bifidobacterium bifidum* MCC1870 (NITE BP-02433), or *Bifidobacterium longum* subsp. *longum* MCC1110 (NITE BP-02430). Hereafter, these five kinds of novel *Bifidobacterium* bacteria may be correctively referred to as "novel *Bifidobacterium* bacterium (or bacteria) of the present invention". *Bifidobacterium longum* subsp. *longum* may be referred to simply as *Bifidobacterium longum*.

The novel *Bifidobacterium* bacteria of the present invention are bacteria separated from human feces as a separation source. In order to investigate genetic characteristics of the novel *Bifidobacterium* bacteria of the present invention, 16S rRNA gene nucleotide sequences thereof were identified in a conventional manner. Homology search of the nucleotide sequences was performed for 16S rRNA gene nucleotide sequence of each *Bifidobacterium* bacterium by BLAST analysis in the database of U.S. National Center of Biotechnology Information (NCBI).

As a result, *Bifidobacterium bifidum* MCC1092 was confirmed to show a nucleotide sequence homology of 99.1% to KCTC3202, which is a type strain of *Bifidobacterium bifidum*, and to be a *Bifidobacterium* bacterium belonging to *Bifidobacterium bifidum*.

*Bifidobacterium bifidum* MCC1319 was confirmed to show a nucleotide sequence homology of 99.0% to KCTC3202, which is a type strain of *Bifidobacterium bifidum*, and to be a *Bifidobacterium* bacterium belonging to *Bifidobacterium bifidum*.

*Bifidobacterium bifidum* MCC1868 was confirmed to show a nucleotide sequence homology of 99.1% to KCTC3202, which is a type strain of *Bifidobacterium bifidum*, and to be a *Bifidobacterium* bacterium belonging to *Bifidobacterium bifidum*.

*Bifidobacterium bifidum* MCC1870 was confirmed to show a nucleotide sequence homology of 99.1% to KCTC3202, which is a type strain of *Bifidobacterium bifidum*, and to be a *Bifidobacterium* bacterium belonging to *Bifidobacterium bifidum*.

*Bifidobacterium longum* subsp. *longum* MCC1110 was confirmed to show a nucleotide sequence homology of 98.8% to KCTC3128, which is a type strain of *Bifidobacterium longum* subsp. *longum*, and to be a *Bifidobacterium* bacterium belonging to *Bifidobacterium longum* subsp. *longum*.

*Bifidobacterium bifidum* MCC1092 was deposited at the independent administrative agency, National Institute of Technology and Evaluation, NITE Patent Microorsganism Depositary (#122, 2-5-8 Kazusakamatari, Kisarazu-shi, Chiba-ken, 292-0818, Japan) on Feb. 21, 2017 (Heisei 29) as an international deposit according to the provisions of the Budapest Treaty, and given an accession number NITE BP-02429.

*Bifidobacterium bifidum* MCC1319 was deposited at the independent administrative agency, National Institute of Technology and Evaluation, NITE Patent Microorganisms Depositary (#122, 2-5-8 Kazusakamatari, Kisarazu-shi, Chiba-ken, 292-0818, Japan) on Feb. 21, 2017 (Heisei 29) as an international deposit according to the provisions of the Budapest Treaty, and given an accession number NITE BP-02431.

Bifidobacterium bifidum MCC1868 was deposited at the independent administrative agency, National Institute of Technology and Evaluation, NITE Patent Microorganisms Depositary (#122, 2-5-8 Kazusakamatari, Kisarazu-shi, Chiba-ken, 292-0818, Japan) on Feb. 21, 2017 (Heisei 29) as an international deposit according to the provisions of the Budapest Treaty, and given an accession number NITE BP-02432 is given.

Bifidobacterium bifidum MCC1870 was deposited at the independent administrative agency, National Institute of Technology and Evaluation, NITE Patent Microorganisms Depositary (#122, 2-5-8 Kazusakamatari, Kisarazu-shi, Chiba-ken, 292-0818, Japan) on Feb. 21, 2017 (Heisei 29) as an international deposit according to the provisions of the Budapest Treaty, and given an accession number NITE NITE BP-02433.

Bifidobacterium longum subsp. longum MCC1110 was deposited at the independent administrative agency, National Institute of Technology and Evaluation, Patent Microorganisms Depositary (#122, 2-5-8 Kazusakamatari, Kisarazu-shi, Chiba-ken, 292-0818, Japan) on Feb. 21, 2017 (Heisei 29) as an international deposit according to the provisions of the Budapest Treaty, and given an accession number NITE BP-02430.

The novel Bifidobacterium bacterium of the present invention is not limited to the aforementioned deposited strains, but may be a bacterium substantially equivalent to any one of the deposited strains. Such a substantially equivalent bacterium refers to a bacterium of the same genus or species as those of the novel Bifidobacterium bacteria of the present invention, which has a high DPP-4 activity or plasmin activity comparable to those of the aforementioned deposited strains. Further, the 16S rRNA gene nucleotide sequence of such a substantially equivalent bacterium shows a homology of 98% or higher, preferably 99% or higher, more preferably 100%, to the nucleotide sequence of 16S rRNA gene of any one of the aforementioned deposited strains, and such a substantially equivalent bacterium preferably has the same bacteriological characteristics as those of any one of the aforementioned deposited strains. The novel Bifidobacterium bacterium of the present invention may be a variant strain bred from any one of the deposited strains or a bacterium substantially equivalent to any one of deposited strains by mutation treatment, gene recombination, selection of a spontaneously mutated strain, or the like, so long as the effect of the present invention is not degraded.

The novel Bifidobacterium bacterium of the present invention or a culture of the Bifidobacterium bacterium can be easily obtained by culturing the Bifidobacterium bacterium in a conventional manner. The culture method is not particularly limited so long as the Bifidobacterium bacterium can proliferate, and the culture can be performed under appropriate conditions determined according to the characteristics of the bacterium. For example, the culture temperature may be 25 to 50° C., preferably 35 to 42° C. The culture is preferably performed under anaerobic conditions. For example, the culture can be performed with supply of anaerobic gas such as carbon dioxide. The culture may also be performed under microaerobic conditions such as those obtainable with stationary liquid culture, or the like.

The medium for culturing the novel Bifidobacterium bacterium of the present invention is not particularly limited, and a medium usually used for culture of Bifidobacterium bacteria can be used. That is, as the carbon source, for example, saccharides such as glucose, galactose, lactose, arabinose, mannose, sucrose, starch, starch hydrolysates, and blackstrap molasses can be used according to the assimilation property. As the nitrogen source, for example, ammonia, ammonium salts such as ammonium sulfate, ammonium chloride, and ammonium nitrate, and nitrates can be used. As inorganic salts, for example, sodium chloride, potassium chloride, potassium phosphate, magnesium sulfate, calcium chloride, calcium nitrate, manganese chloride, ferrous sulfate, and so forth can be used. Organic components such as peptone, soybean flour, degreased soybean meal, meat extract, and yeast extract may also be used.

The novel Bifidobacterium bacterium of the present invention can be used in the form of the bacterium per se, a culture thereof, or a processed cell product thereof, which shall apply also to the agent for decomposing an opioid peptide, composition for decomposing an opioid peptide, agent for decomposing a noncollagenous glycoprotein, and composition for decomposing a noncollagenous glycoprotein described later. That is, a culture obtained after culture may be used as it is, the obtained culture may be used after dilution or concentration, or cells collected from the culture may be used. The novel Bifidobacterium bacterium used in the present invention may consist of live cells or dead cells, or both live cells and dead cells. A processed cell product of the novel Bifidobacterium bacterium may also be used, and examples of the processed cell product include, for example, immobilized cells immobilized with acrylamide, carragheenan, or the like, a disrupted cell product in which cell walls and cell membranes of the Bifidobacterium bacterium cells are partially or completely disrupted in a conventional manner such as by ultrasonication or homogenizer treatment, a centrifugation supernatant (fraction of water-soluble components) of the disrupted product, a fraction obtained by partial purification of the supernatant by ammonium sulfate treatment, or the like, a concentrate of the supernatant, and so forth.

As described above, the novel Bifidobacterium bacterium of the present invention can also be used in the form of a composition. Such a composition is a composition containing any one or two or more kinds of the novel Bifidobacterium bacterium of the present invention, and the content of the novel Bifidobacterium bacterium in the composition is preferably $1 \times 10^6$ to $1 \times 10^{12}$ CFU/g or $1 \times 10^6$ to $1 \times 10^{12}$ CFU/mL, more preferably $1 \times 10^7$ to $1 \times 10^{11}$ CFU/g or $1 \times 10^7$ to $1 \times 10^{11}$ CFU/mL, further preferably $1 \times 10^8$ to $1 \times 10^{10}$ CFU/g or $1 \times 10^8$ to $1 \times 10^{10}$ CFU/mL. When the bacterium consists of dead cells, the unit CFU should be replaced by number of cells (cells). The novel Bifidobacterium bacterium contained in the composition is preferably in the form of powder obtained by concentration and/or lyophilization, or the like of culture of the novel Bifidobacterium bacterium.

Another aspect of the present invention is a method for producing the composition comprising the step of adding the novel Bifidobacterium bacterium of the present invention. That is, the production method is a method for producing a food or drink composition comprising the step of adding the novel Bifidobacterium bacterium of the present invention to a food raw material. The production method is also a method for producing a pharmaceutical composition comprising the step of mixing the novel Bifidobacterium bacterium with a base. In the production method, the novel Bifidobacterium bacterium may be added after it is cultured, and concentrated or lyophilized, or the production method may comprises the step of culturing the novel Bifidobacterium bacterium after adding it.

<Agent for Decomposing an Opioid Peptide or Composition for Decomposing Opioid Peptide>

In the present invention, the agent for decomposing an opioid peptide is used in order to decompose an opioid peptide mainly derived from a food, and contains the novel *Bifidobacterium* bacterium of the present invention, a culture of the bacterium, and/or a processed cell product of the bacterium as an active ingredient.

The agent for decomposing an opioid peptide of the present invention may contain other ingredients so long as it contains the novel *Bifidobacterium* bacterium of the present invention, a culture of the bacterium, and/or a processed cell product of the bacterium as an active ingredient. That is, the agent for decomposing an opioid peptide of the present invention may also be in the form of a composition for decomposing an opioid peptide. Therefore, one aspect of the present invention is a composition for decomposing an opioid peptide, which contains the novel *Bifidobacterium* bacterium of the present invention, a culture of the bacterium, and/or a processed cell product of the bacterium as an active ingredient.

In the present invention, the opioid peptide is a peptide that binds with an opioid receptor to exhibit various physiological activities. The opioid peptides include endogenous opioid peptides synthesized in the living bodies, and exogenous opioid peptides other than the endogenous opioid peptides. The opioid peptide referred to in the present invention is preferably an exogenous opioid peptide, more preferably an opioid peptide derived from a food. Examples of the opioid peptide derived from a food include β-casomorphin derived from milk, gliadorphin derived from wheat, and so forth.

It is known that such an opioid peptide is decomposed by a specific enzyme, and specifically dipeptidyl peptidase-4 (DPP-4), and so forth are known. Dipeptidyl aminopeptidase is an exopeptidase having an activity of cleaving a dipeptide from the end of a protein or peptide on the amino terminus side, and it is known as an enzyme having an activity for decomposing casomorphins (G. Puschel et al., Eur. J. Biochem., 126 (2), pp. 359-365, 1982).

In the present invention, the *Bifidobacterium* bacterium of the present invention, a culture of the bacterium, and/or a processed cell product of the bacterium has the same enzymatic activity as that of DPP-4, a kind of dipeptidyl aminopeptidase (dipeptidyl aminopeptidase activity), and therefore can decompose an opioid peptide.

The "DPP-4 activity" referred to in this description means an exopeptidase activity for cleaving a dipeptide on the amino terminus side of a protein or peptide as a substrate specific to DPP-4 to decompose the substrate. Examples of the substrate specific to DPP-4 include a protein and peptide having a proline or alanine residue as the second amino acid residue from the amino terminus. In the present invention, the DPP-4 activity of the *Bifidobacterium* bacterium can be confirmed by, for example, the following method.

That is, the activity can be confirmed by measuring fluorescence intensity of a culture obtained by culturing the *Bifidobacterium* bacterium in a medium containing a fluorescent substrate specific to DPP-4. Concentration of a fluorescent substance originating from the fluorescent substrate in the culture can be calculated from the fluorescence intensity of the culture using a calibration curve representing the relationship between the fluorescence intensity and the concentration of the fluorescent substance, and the DPP-4 activity of the *Bifidobacterium* bacterium can be determined in terms of enzyme unit (U), with which the activity for producing 1 nmol of the fluorescent substance in 1 minute is represented as 1 U.

Specifically, cells are separated from a culture of the *Bifidobacterium* bacterium, and suspended in a PBS solution to prepare a suspension, the suspension is diluted to adjust the turbidity (OD600) thereof to be 0.1, then H-Gly-Pro-AMC·HBr (produced by BACHEM), which is a fluorescent substrate specific to DPP-4, is added, anaerobic culture is performed at 37° C. for 60 minutes, then after completion of the culture, fluorescence intensity of the culture is measured with an excitation wavelength of 380 nm and measurement wavelength of 460 nm using a fluorometry apparatus such as Microplate Reader SH-9000 (produced by Corona Electric), and the DPP-4 activity can be determined from the measured fluorescence intensity of the culture.

In the present invention, if the DPP-4 activity of the *Bifidobacterium* bacterium is 0.5 mU or higher, preferably 1.0 mU or higher, the opioid peptide decomposition effect of the present invention can be favorably exhibited.

Another aspect of the present invention is use of the novel *Bifidobacterium* bacterium, a culture of the bacterium, and/or a processed cell product of the bacterium for the manufacture of the agent for decomposing an opioid peptide or composition for decomposing an opioid peptide.

Still another aspect of the present invention is use of the novel *Bifidobacterium* bacterium, a culture of the bacterium, and/or a processed cell product of the bacterium in decomposition of an opioid peptide.

Still another aspect of the present invention is the novel *Bifidobacterium* bacterium, a culture of the bacterium, and/or a processed cell product of the bacterium, which is used for decomposing an opioid peptide.

Still another aspect of the present invention is the novel *Bifidobacterium* bacterium, a culture of the bacterium, and/or a processed cell product of the bacterium, which is used for amelioration, prevention or treatment of a disease that can be ameliorated, prevented or treated by decomposition of an opioid peptide.

Still another aspect of the present invention is a method for decomposing an opioid peptide or a method for ameliorating, preventing or treating a disease that can be ameliorated, prevented or treated by decomposition of an opioid peptide, which comprises administering the novel *Bifidobacterium* bacterium, a culture of the bacterium, and/or a processed cell product of the bacterium to a mammal.

Still another aspect of the present invention is a method for decomposing an opioid peptide or a method for ameliorating, preventing or treating a disease that can be ameliorated, prevented or treated by decomposition of an opioid peptide, which comprises administering an agent for decomposing an opioid peptide or composition for decomposing an opioid peptide containing the aforementioned novel *Bifidobacterium* bacterium, a culture of the bacterium, and/or a processed cell product of the bacterium as an active ingredient to a mammal.

<Agent for Decomposing a Noncollagenous Glycoprotein or Composition for Decomposing Noncollagenous Glycoprotein>

According to the present invention, the agent for decomposing a noncollagenous glycoprotein contains the novel *Bifidobacterium* bacterium of the present invention, a culture of the bacterium, and/or a processed cell product of the bacterium as an active ingredient, and exhibits a noncollagenous glycoprotein decomposition effect on the basis of an enzymatic activity of the novel *Bifidobacterium* bacterium and/or a culture of the bacterium similar to that of plasmin (plasmin activity).

The agent for decomposing a noncollagenous glycoprotein of the present invention may contain other ingredients so long as it contains the novel *Bifidobacterium* bacterium of the present invention, a culture of the bacterium, and/or a processed cell product of the bacterium as an active ingredient. That is, the agent for decomposing a noncollagenous glycoprotein of the present invention may also be in the form of a composition for decomposing a noncollagenous glycoprotein. Therefore, one aspect of the present invention is a composition for decomposing a noncollagenous glycoprotein, which contains the novel *Bifidobacterium* bacterium of the present invention, a culture of the bacterium, and/or a processed cell product of the bacterium as an active ingredient.

In the present invention, examples of the noncollagenous glycoprotein include cell adhesion molecules that form the reticular structure of the extracellular matrix surrounding cells or tissues, which may be in the form of monomer, or oligomer or polymer. Specific examples include fibrin (also called "stabilized fibrin"), fibrin polymer, fibrin monomer, fibrin clot, fibrinogen, fibronectin, vitronectin, laminin, nidogen, teneicin, thrombospondin, von Willebrand factor, osteopontin, and so forth. Among these, fibrin, fibrinogen, fibronectin, laminin, and plasminogen are preferred, and fibrinogen is more preferred.

The "plasmin activity" referred to here means an endopeptidase activity for cleaving a non-terminus peptide bond of a protein or peptide as a substrate specific to plasmin to decompose the substrate.

Plasmin usually exists in blood as plasminogen, which is an inactive precursor, and plasminogen is converted into plasmin by cleavage of a specific peptide bond of plasminogen by the plasminogen activator (PA) and thereby activated to exhibit the enzymatic activity. However, the *Bifidobacterium* bacterium of the present invention can exhibit the plasmin activity without further presence of plasminogen and plasminogen activator (PA).

In the present invention, the plasmin activity of the *Bifidobacterium* bacterium can be confirmed by, for example, the following method.

That is, the plasmin activity can be confirmed by measuring fluorescence intensity of a culture obtained by culturing the *Bifidobacterium* bacterium in a mixture containing a fluorescence substrate specific to plasmin. The concentration of the fluorescent substance in the culture can be calculated from the fluorescence intensity of the culture using a calibration curve representing the relationship between the concentration of the fluorescent substance originating from the fluorescent substrate and the fluorescence intensity, and the plasmin activity of the *Bifidobacterium* bacterium can be determined in terms of enzyme unit (U), with which the activity for producing 1 nmol of the fluorescent substance in 1 minute is represented as 1 U.

Specifically, cells are separated from the culture of the *Bifidobacterium* bacterium, and suspended in a PBS solution to prepare a suspension, the suspension is diluted to adjust the turbidity (OD600) thereof to be 0.1, then Boc-Val-Leu-Lys-AMC (produced by BACHEM), which is a fluorescent substrate specific to plasmin, is added, anaerobic culture is performed at 37° C. for 60 minutes, then after completion of the culture, fluorescence intensity of the culture is measured with an excitation wavelength of 380 nm and measurement wavelength of 460 nm using a fluorometry apparatus such as Microplate Reader SH-9000 (produced by Corona Electric), and the plasmin activity of the *Bifidobacterium* bacterium can be determined from the measured fluorescence intensity of the culture.

According to the present invention, if the plasmin activity is preferably 50 μU or higher, more preferably 80 μU or higher, the noncollagenous glycoprotein decomposition effect of the present invention can be favorably exhibited.

Another aspect of the present invention is use of the novel *Bifidobacterium* bacterium, a culture of the bacterium, and/or a processed cell product of the bacterium for the manufacture of the agent for decomposing a noncollagenous glycoprotein or composition for decomposing a noncollagenous glycoprotein.

Still another aspect of the present invention is use of the novel *Bifidobacterium* bacterium, a culture of the bacterium, and/or a processed cell product of the bacterium in decomposition of a noncollagenous glycoprotein.

Still another aspect of the present invention is the novel *Bifidobacterium* bacterium, a culture of the bacterium, and/or a processed cell product of the bacterium, which is used for decomposition of a noncollagenous glycoprotein.

Still another aspect of the present invention is the novel *Bifidobacterium* bacterium, a culture of the bacterium, and/or a processed cell product of the bacterium, which is used for amelioration, prevention or treatment of a disease that can be ameliorated, prevented or treated by decomposition of a noncollagenous glycoprotein.

Still another aspect of the present invention is a method for decomposing a noncollagenous glycoprotein or a method for ameliorating, preventing or treating a disease that can be ameliorated, prevented or treated by decomposition of a noncollagenous glycoprotein, which comprises administering the novel *Bifidobacterium* bacterium, a culture of the bacterium, and/or a processed cell product of the bacterium to a mammal.

Still another aspect of the present invention is a method for decomposing a noncollagenous glycoprotein or a method for ameliorating, preventing or treating a disease that can be ameliorated, prevented or treated by decomposition of a noncollagenous glycoprotein, which comprises administering an agent for decomposing a noncollagenous glycoprotein or composition for decomposing a noncollagenous glycoprotein containing the aforementioned novel *Bifidobacterium* bacterium, a culture of the bacterium, and/or a processed cell product of the bacterium as an active ingredient to a mammal.

<Pharmaceutical Composition>

The novel *Bifidobacterium* bacterium of the present invention, a culture of the bacterium and/or a processed cell product of the bacterium can be used as a pharmaceutical composition.

It is known that if an opioid peptide is not decomposed within the alimentary tract, and is absorbed by living bodies, it affects conditions of autism, Asperger's syndrome, Rett's disorder, childhood disintegrative disorder, and so forth (Patent document 1). For example, it has been reported that a child with autism showing a higher urinary concentration of β-casomorphin, which is an opioid peptide, shows a correspondingly higher childhood autism rating scale (CARS) value (O. Sokolov et al., Peptides, 56, pp. 68-71, 2014). It has also been reported that the blood β-casomorphin concentration of an infant developing an apparent life threatening event (ALTE) such as apnea is higher than that of a healthy infant, and the activity of dipeptidyl peptidase 4 (DPP-4), which is an enzyme that decomposes β-casomorphin, of such an infant is lower than that of a healthy infant (J. Wasilewska et al., Neuropeptides, 45, pp. 189-195, 2011).

Therefore, since the novel *Bifidobacterium* bacterium of the present invention, a culture of the bacterium, and/or a processed cell product of the bacterium has an opioid peptide decomposition action based on the DPP-4 activity, the pharmaceutical composition of the present invention can be used for prevention or treatment of a disease that can be prevented or treated by decomposition of an opioid peptide. Examples of such a disease include, for example, autism, Asperger's syndrome, Rett's disorder, childhood disintegrative disorder, sleep apnea, and so forth, and the pharmaceutical composition of the present invention can be used as a pharmaceutical composition for prevention and/or treatment of such diseases.

Another aspect of the present invention is a method for preventing or treating a disease that can be prevented or treated by decomposition of an opioid peptide, which comprises administering the novel *Bifidobacterium* bacterium, a culture of the bacterium, and/or a processed cell product of the bacterium to a mammal. Still another aspect of the present invention is a method for preventing or treating a disease that can be prevented or treated by decomposition of an opioid peptide, which comprises administering a composition for decomposing an opioid peptide containing the aforementioned novel *Bifidobacterium* bacterium, a culture of the bacterium, and/or a processed cell product of the bacterium as an active ingredient to a mammal. Examples of the objective disease of these aspects include, for example, autism, Asperger's syndrome, Rett's disorder, childhood disintegrative disorder, sleep apnea, and so forth.

It is also known that plasmin is effective for fibrinolytic therapy of ischemic injuries such as cerebral infarction, arteriovenous thrombosis in extremities, pulmonary infarction, and cerebral sinus thrombosis on the basis of the decomposition effect for fibrinogen, which is a noncollagenous glycoprotein (Non-patent document 3).

Plasmin is also used for chemical vitrectomy, in which vitreous detachment is required, on the basis of the decomposition effect for a noncollagenous glycoprotein such as fibronectin, which constitutes the vitreous body of eyes, for such diseases of eyes as retinal detachment, retinal laceration, vitreous hemorrhage, diabetic vitreous hemorrhage, proliferative diabetic retinopathy, age-related macular degeneration, macular hole, vitreomacular traction, fibrin deposition, occlusion of retinal vein, occlusion of retinal artery, glaucoma, and retinitis pigmentosa (Japanese Patent Laid-open (KOHYO) No. 2006-518708).

Therefore, since the novel *Bifidobacterium* bacterium, a culture of the bacterium, and/or a processed cell product of the bacterium has a noncollagenous glycoprotein decomposition effect based on the plasmin activity, the pharmaceutical composition of the present invention can be used for prevention or treatment of a disease that can be prevented or treated by decomposition of a noncollagenous glycoprotein. Examples of such a disease include, for example, ischemic injuries such as cerebral infarction, arteriovenous thrombosis in extremities, pulmonary infarction, and cerebral sinus thrombosis, diseases of eyes that require vitreous detachment such as retinal detachment, retinal laceration, vitreous hemorrhage, diabetic vitreous hemorrhage, proliferative diabetic retinopathy, age-related macular degeneration, macular hole, vitreomacular traction, fibrin deposition, occlusion of retinal vein, occlusion of retinal artery, glaucoma, and retinitis pigmentosa, and so forth, and the pharmaceutical composition of the present invention can be used as a pharmaceutical composition for prevention and/or treatment of these diseases.

Another aspect of the present invention is a method for preventing or treating a disease that can be prevented or treated by decomposition of a noncollagenous glycoprotein, which comprises administering the novel *Bifidobacterium* bacterium, a culture of the bacterium, and/or a processed cell product of the bacterium to a mammal. Still another aspect of the present invention is a method for preventing or treating a disease that can be prevented or treated by decomposition of a noncollagenous glycoprotein, which comprises administering a pharmaceutical composition for decomposing a noncollagenous glycoprotein containing the aforementioned novel *Bifidobacterium* bacterium, a culture of the bacterium, and/or a processed cell product of the bacterium as an active ingredient to a mammal. Examples of the diseases as the object of these aspects include, for example, ischemic injuries such as cerebral infarction, arteriovenous thrombosis in extremities, pulmonary infarction, and cerebral sinus thrombosis, diseases of eyes that require vitreous detachment such as retinal detachment, retinal laceration, vitreous hemorrhage, diabetic vitreous hemorrhage, proliferative diabetic retinopathy, age-related macular degeneration, macular hole, vitreomacular traction, fibrin deposition, occlusion of retinal vein, occlusion of retinal artery, glaucoma, and retinitis pigmentosa, and so forth.

Since the pharmaceutical composition of the present invention uses the novel *Bifidobacterium* bacterium of the present invention, which also exists in human intestines, a culture of the bacterium, and/or a processed cell product of the bacterium as an active ingredient, it is expected to hardly provide side reactions even when it is continuously administered for a long period of time.

When the novel *Bifidobacterium* bacterium of the present invention, a culture of the bacterium, and/or a processed cell product of the bacterium is used as a pharmaceutical composition, the pharmaceutical composition may be orally administered or parenterally administered, and it can be appropriately prepared in a desired dosage form depending on the administration method. For example, in the case of oral administration, it can be prepared in the form of solid preparation such as powder, granule, tablet, and capsule, liquid agent such as solution, syrup, suspension, and emulsion, or the like. In the case of parenteral administration, it can be prepared in the form of suppository, ointment, eye drop, or the like.

When the pharmaceutical composition is prepared, such ingredients as excipient, pH adjustor, colorant and corrigent, which are usually used for preparation of pharmaceutical compositions, can be used in addition to the novel *Bifidobacterium* bacterium of the present invention, a culture of the bacterium and/or a processed cell product of the bacterium. The pharmaceutical composition of the present invention may use the novel *Bifidobacterium* bacterium, a culture of the bacterium, and/or a processed cell product of the bacterium together with a known ingredient or ingredient to be found in future having an effect for preventing and/or treating a disease in which an opioid peptide involved, or a disease on which decomposition of a noncollagenous glycoprotein effectively acts, so long as the effect of the present invention is not degraded.

The pharmaceutical composition can be prepared by an appropriate known method depending on the dosage form thereof. When the pharmaceutical composition is prepared, the pharmaceutical composition may be prepared by adding a carrier for pharmaceutical composition.

Although intake or dose of the pharmaceutical composition of the present invention can be appropriately selected depending on the dosage form thereof, the daily intake or dose per 1 kg of body weight of the novel *Bifidobacterium* bacterium of the present invention is, for example, preferably $1\times10^6$ to $1\times10^{12}$ CFU/kg/day, more preferably $1\times10^7$ to $1\times10^{11}$ CFU/kg/day, further preferably $1\times10^8$ to $1\times10^{10}$ CFU/kg/day.

When a culture of the novel *Bifidobacterium* bacterium of the present invention, or a processed cell product of the bacterium is used, intake or dose thereof is preferably such an intake or dose that the intake or the dose of the novel *Bifidobacterium* bacterium of the present invention is within any of the ranges mentioned above.

Although content of the novel *Bifidobacterium* bacterium of the present invention in the pharmaceutical composition of the present invention can be appropriately selected according to the intake mentioned above, it is, for example, $1\times10^6$ to $1\times10^{12}$ CFU/g or $1\times10^6$ to $1\times10^{12}$ CFU/mL, preferably $1\times10^7$ to $1\times10^{11}$ CFU/g or $1\times10^7$ to $1\times10^{11}$ CFU/mL, more preferably $1\times10^8$ to $1\times10^{10}$ CFU/g or $1\times10^8$ to $1\times10^{10}$ CFU/mL.

When a culture of the novel *Bifidobacterium* bacterium of the present invention, or a processed cell product of the bacterium is used, the content thereof is preferably such a content that the content of the novel *Bifidobacterium* bacterium of the present invention is within any of the ranges mentioned above.

CFU contained in the units mentioned above is an abbreviation of colony forming unit. When the bacterium cells consist of dead cells, the amount thereof can be represented in terms of number of cells (cells) instead of CFU.

As the aforementioned carrier for pharmaceutical composition, various organic or inorganic carriers can be used depending on the dosage form. In the case of solid preparation, examples of the carrier include, for example, excipient, binder, disintegrating agent, lubricant, stabilizer, corrigent, and so forth.

Examples of excipient include, for example, sugar and derivatives thereof such as lactose, sucrose, glucose, mannitol, and sorbitol; starch and derivatives thereof such as corn starch, potato starch, pregelatinized starch, dextrin, and carboxymethyl starch; cellulose and derivatives thereof such as crystalline cellulose, hydroxypropylcellulose, hydroxypropylmethylcellulose, carboxymethylcellulose and carboxymethylcellulose calcium; gum arabic; dextran; pullulan; silicate and derivatives thereof such as light silicic anhydride, synthetic aluminum silicate and magnesium metasilicate aluminate; phosphate and derivatives thereof such as calcium phosphate; carbonate derivatives such as calcium carbonate; sulfate derivatives such as calcium sulfate, and so forth.

Examples of binder include, in addition to the aforementioned excipients, for example, gelatin; polyvinylpyrrolidone; Macrogol, and so forth.

Examples of disintegrating agent include, in addition to the aforementioned excipients, for example, chemically modified starch or cellulose derivatives such as croscarmellose sodium, and carboxymethylstarch sodium, crosslinked polyvinylpyrrolidone, and so forth.

Examples of lubricant include, for example, talc; stearic acid; stearic acid metal salts such as calcium stearate and magnesium stearate; colloidal silica; Veegum; waxes such as spermaceti; boric acid; glycols; carboxylic acids such as fumaric acid and adipic acid; carboxylic acid sodium salts such as sodium benzoate; sulfates such as sodium sulfate; leucine; laurylsulfates such as sodium laurylsulfate and magnesium laurylsulfate; silicic acids such as silicic anhydride and silicic acid hydrate; starch derivatives, and so forth.

Examples of stabilizer include, for example, p-hydroxybenzoic acid esters such as methylparaben and propylparaben; alcohols such as chlorobutanol, benzyl alcohol and phenylethyl alcohol; benzalkonium chloride; acetic anhydride; sorbic acid, and so forth.

Examples of corrigent include, for example, sweetener, acidulant, perfume, and so forth.

Examples of the carrier used for liquids for oral administration include solvents such as water, corrigents, and so forth.

<Food or Drink Composition>

The novel *Bifidobacterium* bacterium of the present invention, a culture of the bacterium and/or a processed cell product of the bacterium can also be used as a food or drink composition. The food or drink composition of the present invention may be produced by adding the novel *Bifidobacterium* bacterium of the present invention, a culture of the bacterium, and/or a processed cell product of the bacterium to a known food or drink, or may be prepared as a novel food or drink by adding the novel *Bifidobacterium* bacterium of the present invention, a culture of the bacterium and/or a processed cell product of the bacterium to a raw material of the food or drink. After the novel *Bifidobacterium* bacterium of the present invention is added to a raw material of a food or drink, the step of culturing the bacterium can also be performed.

Form of the food or drink composition of the present invention is not particularly limited, and it may be in the form of liquid, paste, solid, powder, or the like. Examples include tablet confectioneries, liquid diets, feeds (including feeds for pets), and so forth, as well as, for example, flour products, ready-to-eat foods; processed agricultural products, processed marine products, processed livestock products, milks and dairy products, oils and fats, basic seasonings, complex seasonings and foods, frozen foods, confectioneries, beverages, other commercial foods, and so forth. So long as the effect of the present invention is not degraded, a known ingredient or ingredient to be found in the future that has a probiotics effect or assists a probiotics effect may be used in the food or drink composition of the present invention. The food or drink composition of the present invention may contain, for example, various proteins such as whey proteins, casein proteins, soybean proteins or green pea proteins (pea proteins), or a mixture or decomposition product of these; amino acids such as leucine, valine, isoleucine, and glutamine; vitamins such as vitamin B6 and vitamin C; creatine; citric acid; fish oil; or oligosaccharides such as isomaltooligosaccharides, galactooligosaccharides, xylooligosaccharides, soybean oligosaccharides, fructooligosaccharides, and lactulose.

The food or drink composition of the present invention can also be provided and sold as a food or drink with an indication of use thereof (including health use) such as prevention of a disease in which an opioid peptide is involved, or on which decomposition of a noncollagenous glycoprotein effectively acts, amelioration of conditions of such a disease, and/or treatment of such a disease.

The aforementioned term "indication" means all actions for informing consumers the aforementioned use, and any indications reminding or analogizing the aforementioned use fall within the scope of the "indication" referred to in the present invention regardless of purpose and content of the indication, objective article or medium on which the indication is used, and so forth.

The indication is preferably made with an expression that allows consumers to directly recognize the aforementioned use. Specific examples include actions of assigning or delivering commodities including the food or drink on which the aforementioned use is indicated or such commodities having packages on which the aforementioned use is indicated, displaying or importing such commodities, displaying or distributing advertisements, price lists or business papers relating to such commodities on which the aforementioned use is indicated, providing information including those as contents with indicating the aforementioned use by an electromagnetic method (Internet etc.) for the purpose of assigning or delivering such commodities, and so forth.

The indication is preferably an indication approved by the administration etc. (for example, an indication in a form based on an approval, which is qualified on the basis of any of various legal systems provided by the administration). Indications of such contents on packages, containers, catalogues, pamphlets, advertisement materials used at the sales spots such as POPs, and other papers are especially preferred.

Examples of the "indication" include, for example, indications as health food, functional food, enteral nutritive food, food for special dietary uses, food with health claims, food for specified health uses, food with nutrient function claims, food with function claims, quasi-drug, and so forth. Among these, indications approved by the Consumer Affairs Agency, for example, indications approved on the basis of the systems of food for specified health uses, food with nutrient function claims, food with function claims, and similar systems can be especially mentioned. Specific examples include indications as food for specified health uses, indications as food for specified health uses with qualified health claims, indications of influence on body structures and functions, indications of reduction of disease risk claims, indications of functional claims based on scientific evidence, and so forth, and more precisely, typical examples include the indications as food for specified health uses (especially indications of use for health) defined in the Cabinet Office Ordinance concerning approval of indications of special dietary uses provided by the Health Promotion Law, and others (Cabinet Office Ordinance No. 57, Aug. 31, 2009), and similar indications.

Intake of the food or drink composition of the present invention can be appropriately selected. For example, the daily intake per 1 kg of body weight of the novel *Bifidobacterium* bacterium of the present invention is preferably $1 \times 10^6$ to $1 \times 10^{12}$ CFU/kg/day, more preferably $1 \times 10^7$ to $1 \times 10^{11}$ CFU/kg/day, further preferably $1 \times 10^8$ to $1 \times 10^{10}$ CFU/kg/day.

When a culture of the novel *Bifidobacterium* bacterium of the present invention, or a processed cell product of the bacterium is used, intake thereof is preferably such an intake that the intake of the novel *Bifidobacterium* bacterium of the present invention contained in the culture or processed cell product is within any of the ranges mentioned above.

Although content of the novel *Bifidobacterium* bacterium of the present invention in the food or drink composition of the present invention can be appropriately selected according to the intake mentioned above, it may be, for example, $1 \times 10^6$ to $1 \times 10^{12}$ CFU/g or $1 \times 10^6$ to $1 \times 10^{12}$ CFU/mL, preferably $1 \times 10^7$ to $1 \times 10^{11}$ CFU/g or $1 \times 10^7$ to $1 \times 10^{11}$ CFU/mL, more preferably $1 \times 10^8$ to $1 \times 10^{10}$ CFU/g or $1 \times 10^8$ to $1 \times 10^{10}$ CFU/mL. When the bacterium consists of dead cells, CFU should be replaced with number of cells (cells).

When a culture of the novel *Bifidobacterium* bacterium of the present invention, or a processed cell product of the bacterium is used, the content thereof is preferably such a content that the content of the novel *Bifidobacterium* bacterium of the present invention is within any of the ranges mentioned above.

The food or drink composition of the present invention can be used as a food or drink composition for humans or animals.

Since the food or drink composition of the present invention has the opioid peptide decomposition action based on the DPP-4 activity, it can be used for prevention or treatment of a disease that can be prevented or treated by decomposition of an opioid peptide. Examples of such a disease include, for example, diseases in which an opioid peptide is involved, such as autism, Asperger's syndrome, Rett's disorder, childhood disintegrative disorder, and sleep apnea.

Further, since the food or drink composition of the present invention has a noncollagenous glycoprotein decomposition action based on the plasmin activity, it can be used for prevention or treatment of a disease that can be prevented or treated by decomposition of a noncollagenous glycoprotein. Examples of such a disease include, for example, ischemic injuries such as cerebral infarction, arteriovenous thrombosis in extremities, pulmonary infarction, and cerebral sinus thrombosis, as well as diseases of eyes that requires vitrectomy, such as retinal detachment, retinal laceration, vitreous hemorrhage, diabetic vitreous hemorrhage, proliferative diabetic retinopathy, age-related macular degeneration, macular hole, vitreomacular traction, fibrin deposition, occlusion of retinal vein, occlusion of retinal artery, glaucoma, and retinitis pigmentosa.

Plasmin is also used for maturing dairy products, or manufacture of cheese (X. G. Song et al., Journal of Food Science and Technology (Journal of Japanese Society for Food Science and Technology), Vol. 40, No. 4, April, 1993). It is known that plasmin exists as plasminogen in milk of mammals, and mother's milk of a mother who has experienced premature delivery has a plasmin concentration higher than usual. As a result, mother's milk given to a premature baby contains milk peptides at a higher concentration compared with mother's milk given to full term infant (E. Armaforte et al., International Dairy Journal, 20, pp. 715-723, 2010).

Therefore, the food or drink composition of the present invention for decomposing a noncollagenous glycoprotein preferably contains plasminogen, and it can be preferably used as a food material as an additive for promoting maturing of milk products or cheese, powdered infant formula for premature baby, a food material as an additive to mother's milk or foods. Since the food or drink composition of the present invention contains the *Bifidobacterium* bacterium as an active ingredient, it can be safely given even to infants.

EXAMPLES

Hereafter, the present invention will be explained with reference to examples. However, the present invention is not limited by these examples.

Test Example 1

A test for confirming that the *Bifidobacterium* bacteria have the DPP-4 activity was performed.
(1) Preparation of Culture A cell suspension (90 µL) of each of the following seven kinds of *Bifidobacterium* bacteria (five kinds of novel *Bifidobacterium* bacteria and two kinds of known *Bifidobacterium* bacteria), which had been cryopreserved in an aqueous solution containing 1% sodium glutamate and 10% skim milk powder, was added to 3 mL of the MRS liquid medium, and anaerobic culture was carried out at 37° C. for 16 hours so that the cell number of the *Bifidobacterium* bacterium in the culture became 1×10$^9$ CFU/mL. The MRS liquid medium was prepared by dissolving 5.5 g of Difco Lactobacilli MRS Broth (produced by BD), and 50 mg of L-cysteine monohydrochloride monohydrate (produced by Wako Pure Chemical Industries) in pure water so as to obtain a volume of 100 mL, adjusting the solution to pH 6.5 with an HCl aqueous solution, and sterilizing the solution at 121° C. for 15 minutes.

<Five Kinds of Novel *Bifidobacterium* Bacteria>
    *Bifidobacterium bifidum* MCC1092 (NITE BP-02429)
    *Bifidobacterium bifidum* MCC1319 (NITE BP-02431)
    *Bifidobacterium bifidum* MCC1868 (NITE BP-02432)
    *Bifidobacterium bifidum* MCC1870 (NITE BP-02433)
    *Bifidobacterium longum* subsp. *longum* MCC1110 (NITE BP-02430)

<Two Kinds of Known *Bifidobacterium* Bacteria>
    *Bifidobacterium angulatum* ATCC 27535
    *Bifidobacterium animalis* subsp. *animalis* ATCC 25527

(2) Measurement of DPP-4 Activity

Each culture prepared in (1) was centrifuged under the conditions of 4° C. and 5000×g for 30 minutes, then the supernatant was discarded, and the separated cells were suspended in a PBS solution. Each suspension was prepared at a turbidity (OD600) of 0.1, H-Gly-Pro-AMC·HBr (produced by BACHEM), which is a fluorescent substrate specific to DPP-4, was added, and anaerobic culture was performed at 37° C. for 60 minutes. After completion of the culture, the fluorescence intensity of the culture was measured at an excitation wavelength of 360 nm and a measurement wavelength of 460 nm with Microplate Reader SH-9000 (produced by Corona Electric). The unit of the fluorescence intensity was arbitrary unit (a.u.). From the measured fluorescence intensity, the concentration (nM) of the fluorescent substance derived from the fluorescent substrate, aminomethylcoumarin (AMC), in the culture was calculated by using a calibration curve representing relationship between the concentration of AMC and the fluorescence intensity at the measurement wavelength of 460 nm, which was created beforehand. Further, the DPP-4 activity of each *Bifidobacterium* bacterium was calculated from the AMC concentration in terms of the enzyme unit, with which the enzymatic activity for producing 1 nmol of AMC in 1 minute is represented as 1 unit (U).

(3) Results

The fluorescence intensities and DPP-4 activities are shown in Table 1. It was confirmed that all the *Bifidobacterium* bacteria used for the test exhibit the DPP-4 activity. The novel *Bifidobacterium* bacteria of the present invention, *Bifidobacterium bifidum* MCC1092 (NITE BP-02429), *Bifidobacterium bifidum* MCC1319 (NITE BP-02431), *Bifidobacterium bifidum* MCC1868 (NITE BP-02432), *Bifidobacterium bifidum* MCC1870 (NITE BP-02433), and *Bifidobacterium longum* subsp. *longum* MCC1110 (NITE BP-02430), showed high DPP-4 activities higher by more than twice than that of the known *Bifidobacterium* bacterium, *Bifidobacterium angulatum* ATCC 27535, and higher by more than 5 times than that of the known *Bifidobacterium* bacterium, *Bifidobacterium animalis* subsp. *animalis* ATCC 25527. The DPP-4 activity of *Bifidobacterium bifidum* MCC1319 (NITE BP-02431), which showed the highest activity among the novel *Bifidobacterium* bacteria, was 2.88 mU, i.e., it showed the DPP-4 activity about 7 times higher than that of *Bifidobacterium angulatum* ATCC 27535 and about 15 times higher than that of *Bifidobacterium animalis* subsp. *animalis* ATCC 25527.

TABLE 1

|  | Fluorescence intensity (a.u.) | DPP-4 activity (mU) |
|---|---|---|
| *Bifidobacterium bifidum* MCC1092 (NITE BP-02429) | 12092 | 1.18 |
| *Bifidobacterium bifidum* MCC1319 (NITE BP-02431) | 29136 | 2.88 |
| *Bifidobacterium bifidum* MCC1868 (NITE BP-02432) | 11963 | 1.17 |
| *Bifidobacterium bifidum* MCC1870 (NITE BP-02433) | 15482 | 1.52 |
| *Bifidobacterium longum* subsp. *longum* MCC1110 (NITE BP-02430) | 10416 | 1.01 |
| *Bifidobacterium angulatum* ATCC27535 | 4511 | 0.42 |
| *Bifidobacterium animalis* subsp. *animalis* ATCC25527 | 2177 | 0.19 |

Test Example 2

A test for confirming that the *Bifidobacterium* bacteria have the plasmin activity was performed.

(1) Preparation of Culture

Cultures of the following seven kinds of *Bifidobacterium* bacteria (five kinds of novel *Bifidobacterium* bacteria and two kinds of known *Bifidobacterium* bacteria) were prepared in the same manner as that of "(1) Preparation of culture" of Test Example 1.

<Five Kinds of Novel *Bifidobacterium* Bacteria>
    *Bifidobacterium bifidum* MCC1092 (NITE BP-02429)
    *Bifidobacterium bifidum* MCC1319 (NITE BP-02431)
    *Bifidobacterium bifidum* MCC1868 (NITE BP-02432)
    *Bifidobacterium bifidum* MCC1870 (NITE BP-02433)
    *Bifidobacterium longum* subsp. *longum* MCC1110 (NITE BP-02430)

<Two Kinds of Known *Bifidobacterium* Bacteria>
    *Bifidobacterium angulatum* ATCC 27535
    *Bifidobacterium animalis* subsp. *animalis* ATCC 25527

(2) Measurement of Plasmin Activity

Each culture prepared in (1) was centrifuged under the conditions of 4° C. and 5000×g for 30 minutes, then the supernatant was discarded, and the separated cells were suspended in a PBS solution. Each suspension was prepared at a turbidity (OD600) of 0.1, Boc-Val-Leu-Lys-AMC acetate (produced by BACHEM), which is a fluorescent substrate specific to plasmin, was added, and anaerobic culture was performed at 37° C. for 60 minutes. After completion of the culture, the fluorescence intensity of the culture was measured at an excitation wavelength of 360 nm and a measurement wavelength of 460 nm with Microplate Reader SH-9000 (produced by Corona Electric). From the measured fluorescence intensity, the concentration of the fluorescent substance derived from the fluorescent substrate, aminomethylcoumarin (AMC), in the culture was calculated by using a calibration curve representing relationship between the concentration of the fluorescent substance and the fluorescence intensity at the measurement wavelength of 460 nm, which was created beforehand, and the plasmin activity of each *Bifidobacterium* bacterium was calculated from the concentration in terms of the enzyme unit, with which the enzymatic activity for producing 1 nmol of AMC in 1 minute is represented as 1 unit (U).

(3) Results

The fluorescence intensities and plasmin activities are shown in Table 2. It was confirmed that all the *Bifidobacterium* bacteria used for the test exhibit the plasmin activity. The novel *Bifidobacterium* bacteria of the present invention, *Bifidobacterium bifidum* MCC1092 (NITE BP-02429), *Bifidobacterium bifidum* MCC1319 (NITE BP-02431), *Bifidobacterium bifidum* MCC1868 (NITE BP-02432), *Bifidobacterium bifidum* MCC1870 (NITE BP-02433), and *Bifidobacterium longum* subsp. *longum* MCC1110 (NITE BP-02430), showed high plasmin activities higher by more than 2.5 times than that of the known *Bifidobacterium* bacterium, *Bifidobacterium angulatum* ATCC 27535, and higher by more than 4 times than that of the known *Bifidobacterium* bacterium, *Bifidobacterium animalis* subsp. *animalis* ATCC 25527. The plasmin activity of *Bifidobacterium bifidum* MCC1319 (NITE BP-02431), which showed the highest activity among the novel *Bifidobacterium* bacteria, was 1072 µU, i.e., it showed a markedly high plasmin activity about 40 times higher than that of *Bifidobacterium angulatum* ATCC 27535 and about 63 times higher than that of *Bifidobacterium animalis* subsp. *animalis* ATCC 25527.

TABLE 2

| | Fluorescence intensity (a.u.) | Plasmin activity (µU) |
|---|---|---|
| *Bifidobacterium bifidum* MCC1092 (NITE BP-02429) | 1820 | 158 |
| *Bifidobacterium bifidum* MCC1319 (NITE BP-02431) | 12100 | 1072 |
| *Bifidobacterium bifidum* MCC1868 (NITE BP-02432) | 4231 | 372 |
| *Bifidobacterium bifidum* MCC1870 (NITE BP-02433) | 4432 | 390 |
| *Bifidobacterium longum* subsp. *longum* MCC1110 (NITE BP-02430) | 957 | 81 |
| *Bifidobacterium angulatum* ATCC27535 | 350 | 27 |
| *Bifidobacterium animalis* subsp. *animalis* ATCC25527 | 229 | 17 |

Preparation Example 1

One or more kinds of bacteria selected from the five kinds of the novel *Bifidobacterium* bacteria used in Test Examples 1 and 2 are added to 3 mL of the MRS liquid medium for each strain or the same MRS liquid medium, anaerobic culture is carried out at 37° C. for 16 hours, and the culture is concentrated and lyophilized to obtain cell powder of the one or more kinds of bacteria. The cell powder of the one or more kinds of bacteria is appropriately mixed with an excipient etc., and the mixture is made into tablets. The tablets are taken every day for three months so that the total intake of the bacteria is $1\times10^6$ to $1\times10^{12}$ cfu/kg of body weight/day.

Intake of the tablets is expected to provide an opioid peptide decomposition effect and/or a noncollagenous glycoprotein decomposition effect.

Preparation Example 2

One or more kinds of bacteria selected from the five kinds of the novel *Bifidobacterium* bacteria used in Test Examples 1 and 2 are added to 3 mL of the MRS liquid medium for each strain or the same MRS liquid medium, anaerobic culture is carried out at 37° C. for 16 hours, and the culture is concentrated and lyophilized to obtain cell powder of the one or more kinds of bacteria. The cell powder of the one or more kinds of bacteria is added to a fermented milk material to obtain fermented milk. The fermented milk is taken every day for at least three months so that the total intake of the bacteria is $1\times10^6$ to $1\times10^{12}$ cfu/kg of body weight/day.

Intake of the fermented milk is expected to provide an opioid peptide decomposition effect and/or a noncollagenous glycoprotein decomposition effect.

Preparation Example 3

A method for producing a powdered infant formula using one or more kinds of bacteria selected from the five kinds of the novel *Bifidobacterium* bacteria used in Test Examples 1 and 2 is shown below.

Desalted milk serum protein powder (10 kg, produced by Milei), milk casein powder (6 kg, produced by Fonterra), lactose (48 kg, produced by Milei), mineral mixture (920 g, produced by Tomita Pharmaceutical), vitamin mixture (32 g, produced by Tanabe Seiyaku), lactulose (500 g, produced by Morinaga Milk Industry), raffinose (500 g, produced by Nippon Beet Sugar Mfg.), and galactooligosaccharide liquid sugar (900 g, produced by Yakult Pharmaceutical Industry) are dissolved in warm water (300 kg), and further dissolved by heating at 90° C. for 10 minutes, modified fat (28 kg, produced by TAIYO YUSHI) is added, and the mixture is homogenized. Then, the mixture is sterilized, concentrated, and spray-dried to prepare powdered infant formula (about 95 kg). To this formula, cell powder obtained by adding one or more kinds of bacteria selected from the five kinds of the novel *Bifidobacterium* bacteria used in Test Examples 1 and 2 to 3 mL of the MRS liquid medium for each strain or the same MRS liquid medium, carrying out anaerobic culture at 37° C. for 16 hours, concentrating and lyophilizing the culture, and triturating the obtained cells with starch (100 g, $1.8\times10^{11}$ cfu/g) to prepare about 95 kg of a bifidobacterium and oligosaccharide-formulated powdered infant formula. If the obtained powdered infant formula is dissolved in water to prepare a liquid infant formula having a total solid concentration of 14% (w/v), which is a normal concentration for milk preparation, the number of the bifidobacteria in the liquid formula is $2.7\times10^9$ cfu/100 ml. Intake of the powdered infant formula obtained as described above is expected to provide an opioid peptide decomposition effect and/or a noncollagenous glycoprotein decomposition effect.

The invention claimed is:

1. A cell powder comprising *Bifidobacterium* bacteria that has been dried, wherein the *Bifidobacterium* bacterium is *Bifidobacterium bifidum* MCC1319 deposited with the National Institute of Technology and Evaluation under the accession number NITE BP-02431.

2. A method for decomposing an opioid peptide selected from the group consisting of ß-casomorphin, gliadorphin, and combinations thereof, which comprises administering to a subject in need thereof a composition comprising the cell powder of claim 1.

3. A method for decomposing a noncollagenous glycoprotein selected from the group consisting of fibrin, fibrinogen, fibronectin, laminin, and plasminogen, which comprises administering to a subject in need thereof a composition comprising the cell powder of claim 1.

4. The cell powder of claim 1, which has been further triturated.

5. The cell powder of claim 1, wherein the *Bifidobacterium* bacteria comprises live cells and/or dead cells; and the amount of *Bifidobacterium* bacteria present in the cell powder is $10^6$ (cfu and/or cells)/gm or more.

6. The cell powder of claim 5, wherein the amount of *Bifidobacterium* bacteria present in the cell powder is $10^{12}$ (cfu and/or cells)/gm or less.

7. The cell powder of claim 1, wherein the *Bifidobacterium* bacteria comprises live cells and/or dead cells.

8. A food comprising the cell powder of claim 1.

9. Milk obtained by fermenting milk with the cell powder of claim 1.

10. Infant formula comprising the cell powder of claim 1 dissolved therein.

11. A drink comprising the cell powder of claim 1 dissolved therein.

\* \* \* \* \*